United States Patent [19]
Ray et al.

[11] Patent Number: 5,354,778
[45] Date of Patent: Oct. 11, 1994

[54] ANTITUMOR COMPOSITIONS AND METHODS OF TREATMENT

[75] Inventors: James E. Ray; John E. Toth; J. Jeffry Howbert, all of Indianapolis, Ind.

[73] Assignee: Eli Lilly and Company, Indianapolis, Ind.

[21] Appl. No.: 37,954

[22] Filed: Mar. 26, 1993

Related U.S. Application Data

[62] Division of Ser. No. 811,483, Dec. 20, 1991, Pat. No. 5,234,955.

[51] Int. Cl.$^5$ .................... A61K 31/18; C07C 311/16
[52] U.S. Cl. ........................................ 514/592; 564/42
[58] Field of Search ................... 514/592, 593; 564/42

[56] References Cited

U.S. PATENT DOCUMENTS

| | | | |
|---|---|---|---|
| 3,083,207 | 3/1963 | Hoehn et al. | 548/490 |
| 3,097,242 | 7/1963 | Hoehn et al. | 564/39 |
| 3,102,115 | 8/1963 | Breuer et al. | 548/503 |
| 3,102,121 | 8/1963 | Breuer et al. | 540/606 |
| 3,736,122 | 5/1973 | Tung et al. | 71/103 |
| 3,849,110 | 11/1974 | Soper et al. | 71/94 |
| 4,845,128 | 7/1989 | Harper et al. | 514/592 |

FOREIGN PATENT DOCUMENTS

| | | |
|---|---|---|
| 1208561 | 7/1986 | Canada . |
| 107214 | 9/1983 | European Pat. Off. . |
| 166615 | 1/1986 | European Pat. Off. . |
| 222475 | 5/1987 | European Pat. Off. . |
| 291269 | 11/1988 | European Pat. Off. . |
| 1240866 | 6/1961 | Fed. Rep. of Germany . |
| 1144259 | 2/1963 | Fed. Rep. of Germany . |
| 1159937 | 12/1963 | Fed. Rep. of Germany . |

OTHER PUBLICATIONS

W. J. Ehlhardt, *Drug Metabolism and Disposition*, 19:370 (1991).
J. J. Howbert, et al., *Synthetic Communications*, 20:3193 (1990).
W. J. Ehlhardt, *Drug Metabolism and Disposition*, 19:366 (1991).
J. J. Howbert, et al., *Journal of Medicinal Chemistry*, 33:2393 (1990).
G. B. Grindey, et al., *Proceedings of the American Association of Cancer Research* 27:277 (Abstract 1099)(1986).
C. W. Taylor, et al., *Journal of Clinical Oncology*, 7:1733 (1989).
J. D. Hainsworth, et al., *Cancer Research*, 49:5217 (1989).
R. Levine, *Diabetes Care*, 7 (Suppl. 1):3–7 (1984).
G. F. Holland, et al., *Journal of Medicinal and Pharmaceutical Chemistry*, 3:99 (1961).
P. J. Houghton, et al., *Cancer Chemotherapy and Pharmacology*, 25:84 (1989).
P. J. Houghton, et al., *Cancer Research*, 50:318 (1990).
P. J. Houghton, et al., *Cancer Research*, 50:664 (1990).
P. J. Houghton, et al., *Biochemical Pharmacology*, 39:1187 (1990).
P. H. Dhahir, et al., In *Proceedings of the 36th ASMS Conference on Mass Spectroscopy and Allied Topics*, pp. 972–973 (1988).
G. F. Holland, *Journal of Organic Chemistry*, 26:1662 (1961).
*Chemical Abstracts*, 52:17180; citing Haack, et al., East German Patent 9688, Apr. 21, 1955.
F. Kurzer, *Chemical Reviews*, 50:1 (1952).
G. B. Grindey, et al., In *Proceedings of the American Association for Cancer Research*, 28:309 (Abstract 1224)(1987).
H. Breuer, et al., *Chimie Therapeutique*, Nov./Dec. 1973:659.
L. J. Lerner, et al., *Metabolism*, 14:578 (1965).
G. Jähnchen, et al., *Zeitschrift Chem.*, 39:305 (1969).
M. Thompson, *Journal of Organic Chemistry*, 49:1700 (1984).
G. Foley, et al., *Cancer*, 18:522 (1965).
C. Goralski, et al., *Journal of Chemical and Engineering Data*, 21:237 (1976).

*Primary Examiner*—Shailendra Kumar
*Attorney, Agent, or Firm*—Paul J. Gaylo; David E. Boone

[57] ABSTRACT

This invention provides certain N-phenyl-N'-substituted phenylsulfonylureas compounds, formulations, and a method for treating susceptible neoplasms in mammals using the sulfonylurea compounds.

8 Claims, No Drawings

ANTITUMOR COMPOSITIONS AND METHODS OF TREATMENT

This application is a division, of application Ser. No. 07/811,483 filed Dec. 20, 1991, now U.S. Pat. No. 5,234,955.

BACKGROUND OF THE INVENTION

According to the American Cancer Society about one of every five deaths from all causes in the united States is from cancer. Although chemotherapy has become one of the principal methods of treating cancer, the rate at which drugs have become available for use in cancer chemotherapy has declined in recent years as reported by Horowitz, et al. "Phase II Testing of Melphalan in Children with Newly Diagnosed Rhabdomyosarcoma: A Model for Anticancer Drug Development", *Journal of Clinical Oncology*, Vol. 6, No. 2, pp. 308–314 (1988). Accordingly, there is a substantial need for new drugs which are effective in inhibiting the growth of tumors.

To be particularly useful, a new chemotherapeutic agent should have a wide spectrum of activity, a large therapeutic index, and be chemically stable and compatible with other agents. Additionally, it would be beneficial for the new agent to have oral activity so that initial treatment and subsequent maintenance therapy is more convenient and less traumatic to the patient.

It has now been found that certain N-phenyl-N'-trisubstitutedphenyl sulfonylureas are useful in the treatment of solid tumors.

Some N,N'-diarylsulfonylureas have been reported as being active antitumor agents, e.g., U.S. Pat. No. 4,845,128 of Harper, et al. (1989) and Grindey et al. Proceedings American Association of Cancer Research, Vol. 27, pp. 277 (1986). Other N,N'-diarylsulfonylureas have also been disclosed as useful in treating tumors, i.e., EPO 222,475 and EPO 291,269. There is no suggestion in these references of the N-phenyl-N'-substitutedphenyl-sulfonylureas of the instant application or that these compounds would be useful as antitumor agents.

None of these references suggest or disclose the antitumor activity of the sulfonylurea compounds of the instant invention. Additionally, there is no suggestion or disclosure of the claimed compounds of the instant invention.

SUMMARY OF THE INVENTION

A method is provided for treating susceptible neoplasms in mammals which comprises administering to a mammal in need of such treatment an effective amount of a compound of the Formula I

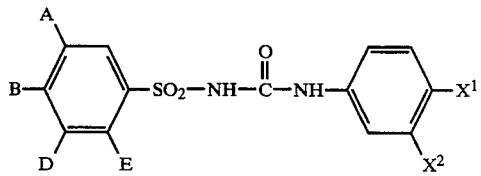

wherein
$X^1$ is halo, $CH_3$ or $CF_3$ and
$X^2$ is hydrogen, halo, or $CF_3$ with the proviso that at least one of $X^1$ and $X^2$ is halo;
A, B, D and E are (a) independently selected from the group consisting of hydrogen, methyl, ethyl, chlorine, bromine and iodine with the proviso that no more than one of A, B, D or E is hydrogen, or (b) E is hydrogen and one of A, B or D is selected from the group consisting of $NH_2$, $NHCH_3$, $N(CH_3)_2$, $N(CH_3)(C_2H_5)$, $N(C_2H_5)_2$, or $OCH_3$ and the remaining of A, B or D are selected from (a), or (c) E is hydrogen and A and B or B and D together are $(CH_2)_n$ or $CH=CH(CH_2)_{n-2}$ wherein n is 3 or 4 or $(CH=CH)_2$, or $—(CH_2)_p—O—$ where p is 2 or 3, or $—O(CH_2)_qO—$ where q is 1 or 2, or $—(CH=CH)_2—$ and D or A respectively is selected from (a);

and pharmaceutically acceptable salts thereof.

In a further embodiment this invention provides pharmaceutical formulations comprising a compound of Formula I in combination with a suitable pharmaceutical excipient. These formulations are particularly useful in treating mammals suffering from susceptible neoplasms.

In another embodiment this invention involves a method for treating susceptible neoplasms in mammals by administering to the mammal an effective amount of a pharmaceutical formulation which comprises a compound of Formula I in combination with a suitable excipient.

DETAILED DESCRIPTION

The compounds of Formula I can be referred to as derivatives of N-[[(substituted phenyl)amino]carbonyl]-substitutedphenyl sulfonamides. Alternatively the compounds can be referred to as 1- and 3-substituted sulfonylureas or N- and N'-substituted sulfonylureas.

As used herein the term "halo" refers to chlorine, bromine, iodine and fluorine.

Preferred compounds of the instant method are those of Formula I in which $X^1$ is chloro, bromo or $CF_3$, $X^2$ is hydrogen or chloro, A, B and D are independently methyl, ethyl, or halo and E is hydrogen.

Most preferred compounds of the instant method include:
N-[[(4-chlorophenyl)amino]carbonyl]-3,4,5-trimethylbenzene sulfonamide; N-[[(4-bromophenyl)amino]carbonyl]-3,4,5-trimethylbenzenesulfonamide; N-[[(4-trifluoromethylpheny)amino]carbonyl]-3,4,5-trimethylbenzenesulfonamide; N-[[(3,4-dichlorophenyl)amino]carbonyl]-3,4,5-trimethylbenzenesulfonamide; N-[[(4-chlorophenyl)amino]carbonyl]-3,4,5-trichlorobenzene sulfonamide; N-[[(4-chlorophenyl)amino]carbonyl]-4-amino-3,5-dichlorobenzenesulfonamide; N-[[(4-chlorophenyl)amino]-carbonyl]-4-chloro-3,5-dimethylbenzenesulfonamide; N-[[(4-chlorophenyl)amino]carbonyl]-4-(N,N,dimethylamino)3,5-dichlorobenzene-sulfonamide; N-[[(4-chlorophenyl)amino]carbonyl]-3,5-dimethyl-4-methoxybenzenesulfonamide; N-[[(4-chlorophenyl)amino]carbonyl]-3,4,5-trimethoxybenzenesulfonamide; N-[[(4-chlorophenyl)amino]carbonyl]-3,5-dibromo-4-(N-methylamino)benzenesulfonamide; and pharmaceutically acceptable salts thereof.

This invention includes the pharmaceutically acceptable salts of the compounds of Formula I. The compounds of this invention can be contacted with basic materials such as alkali metal— or alkaline earth metal hydroxides, carbonates, and bicarbonates, including sodium hydroxide, potassium hydroxide, lithium hydroxide, calcium hydroxide, sodium bicarbonate, etc., to form the corresponding metal salt such as the sodium, potassium, lithium or calcium salt. Nontoxic organic bases can also be used including primary, secondary and tertiary alkyl amines such as methylamine, triethylamine, ethanolamines and the like.

The compounds of Formula I can be prepared by any of the methods known in the literature. Generally these methods involve either the reaction of a sulfonamide with an isocyanate, reaction of a sulfonylcarbamate with an amine, or the reaction of a sulfonylisocyanate with an amine. A preferred method of preparing the instant compounds involves the reaction of a sulfonamide of Formula IIa

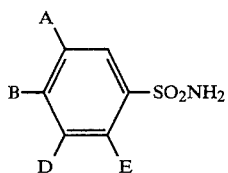

with a basic material to provide the reactive anion of Formula IIb

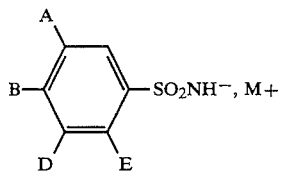

where M+ is a counter ion, prior to contacting an arylisocyanate of Formula III

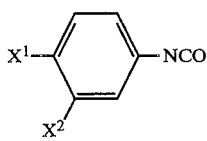

where A, B, D, E, $X^1$, and $X^2$ are the same as previously defined.

A basic material such as sodium hydroxide, potassium hydroxide, lithium hydroxide, sodium methoxide, sodium hydride and the like can be used to contact the sulfonamide to provide the resulting product IIb which can then be contacted with the isocyanate III. The reaction between anion IIb and isocyanate III is usually performed using equal molar amounts of the two reactions although other ratios are operative. The reaction is preferably carried out in a solvent which is nonreactive under the reaction conditions such as benzene, toluene, acetonitrile, ethyl ether, dioxane, or most preferably acetone/water or tetrahydrofuran. The reaction can be carried out at temperatures from about 0° C. normally up to the boiling point of the reaction mixture. At the preferred temperature range of about 0° to 50° C., the reaction is usually complete within two hours. The resulting product is preferably neutralized with an acid such as hydrochloric acid and recovered by filtration. If desired, the product can be purified by any number of methods known to those skilled in the art such as chromatography or crystallization.

The sulfonamide of Formula IIa can be prepared by one of several methods. Generally, the sulfonamides can be prepared by ammonolysis of the appropriate sulfonyl chloride:

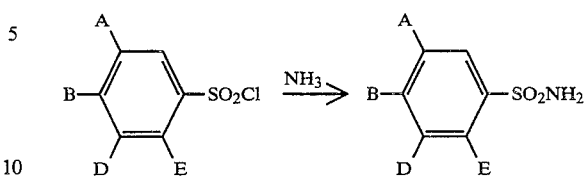

This preparation can be performed using ammonia, with or without a cosolvent such as tetrahydrofuran, or using aqueous ammonia, with or without a cosolvent such as tetrahydrofuran, dichloromethane, etc. Arylthiomethane sulfonamides can be prepared using the method disclosed in *J. Chem. Engineering Data*, 21, 237 (1976). Alkenyl-Sulfonamides can be prepared according to the method disclosed in *J. Ora. Chem.*, 49, 1700 (1984). These articles are incorporated herein by reference in their entirety.

The starting materials and intermediates for these preparations are commercially available or can be readily prepared by the above-described methods or other methods known in the literature.

The terms and abbreviations used in the instant examples have their normal meaning unless otherwise designed, for example, "THF" means tetrahydrofuran; "EE" refers to ethyl ether; "EtOAc" refers to ethyl acetate; "MeOH" refers to methanol; "HOAc" means acetic acid; "°C." refers to degrees celsius; "N" refers to normal or normality; "mmole" refers to millimole; "g" refers to gram; "ml" means milliliter; "M" refers to molar; "NMR" refers to proton nuclear magnetic resonance; and "m.s." refers to mass spectrometry.

The following examples further illustrate the preparation of the compounds of this invention. The examples are provided for purposes of illustration only and are not to be construed as limiting the scope of the instant invention in any way.

EXPERIMENTAL

EXAMPLE 1

N-[[(4-Chlorophenyl)amino]carbonyl]-3,4,5-trimethylbenzene sulfonamide

This compound was prepared by the method of Howbert et. al.[1] from 3,4,5-trimethylbenzenesulfonamide[2] (8.0 g, 40 mmol), 1N aqueous NaOH solution (40 mL, 40 mmol) and p-chlorophenyl isocyanate (7.1 g, 45 mmol) in 40 mL of acetone.

Analysis of the product gave the following results: mp=188–189° C.; $R_f$(1/9 MeOH/CHCl$_3$)=0.47 ; $^1$H NMR (300 MHz, d$_6$-DMSO) δ2.16(s, 3H, CH$_3$), 2.29 (s, 6H, 2CH$_3$), 7.26–7.35 (m, 4H, Ar—H), 7.54 (s, 2H, Ar—H), 8.92 (s, 1H, exchanges with D$_2$O, NH) and 10.6 (bs, 1H, exchanges with D$_2$O, NH); $^{13}$C NMR (75 MHz, d$_6$-DMSO) δ6 15.8, 20.6, 120.9, 126.4, 127.2, 129.0, 136.8, 137.4, 137.5, 141.7 and 149.7; UV(EtOH) λmax(e) 248.8(22496.3) and 205.6(38230.8) nm; IR(KBr) 3362, 1703, 1604, 1541, 1493, 1401, 1334, 1306, 1215, 1151, 1088, 1045, 945, 824, 704 and 675 cm$^{-1}$; FDMS(DMSO) m/e 352, 354 (M+). Anal Calcd for C$_{16}$H$_{17}$Cl$_1$N$_2$O$_3$S$_1$: C, 54.46; H, 4.86; N, 7.94. Found C, 54.26; H, 5.06; N, 7.92.

EXAMPLE 2

N-[[(4-Bromomhenyl)amino]carbonyl]-3,4,5-trimethylbenzenesulfonamide

The method of Example 1 was followed using 3,4,5-trimethylbenzenesulfonamide (2.4 g, 12 mmol), 1N NaOH solution (12 mL, 12 mmol) and p-bromophenyl isocyanate (2.6 g, 13 mmol) to give 3.2 g (68%) of product.

Analysis of the product gave the following results: mp=188–189° C.; $R_f$1/9 MeOH/CHCl$_3$)=0.54 ; $^1$H NMR (300 MHz, d$_6$-DMSO)$\delta$2.16 (s, 3H, CH$_3$), 2.29 (s, 6H, 2CH$_3$) , 7.27 (d, 2H, J=8.1 Hz, Ar—H̲), 7.40 (d, 2H, J=8.1 Hz, Ar—H̲), 7.54 (s, 2H, Ar—H̲), 8.93 (s, 1H, exchanges with D$_2$O, NH̲) and 10.7 (bs, 1H, exchanges with D$_2$O, NH̲); IR (KBr) 3315, 3227, 1703 , 1592, 1526, 1459, 1393 , 1334 , 1302, 1202, 1141, 1105, 1076, 1042, 931, 830 and 648 cm$^{-1}$; FDMS (DMSO) m/e=396, 398 (M+) . Anal Calcd for C$_{16}$H$_{17}$Br$_1$N$_2$O$_3$S$_1$: C, 48.37; H, 4.31; N, 7.05. Found C, 48.27; H, 4.22; N, 6.75.

EXAMPLE 3

N-[[(4-Trifluoromethylphenyl)amino]carbonyl]-3,4,5-trimethylbenzenesulfonamide

The method of Example 1 was followed using 3,4,5-trimethylbenzenesulfonamide (1.5 g, 7.6 mmol), 1N NaOH solution (7.6 mL, 7.6 mmol) and p-trifluoromethylphenyl isocyanate (1.6 g, 8.4 mmol) to yield 1.8 g (61%) of product.

Analysis of the product gave the following results: mp=189–190° C.; $R_f$1/9 MeOH/CHCl$_3$)=0.60 ; $^1$H NMR (300 MHz, d$_6$-DMSO) $\delta$2.17 (s, 3H, CH$_3$), 2.30 (s, 6H, 2CH$_3$), 7.28 (d, 2H, J=8.8 Hz, Ar—H̲), 7.41 (d, 2H, J=8.8 Hz, Ar—H̲), 7.55 (s, 2H, Ar—H̲), 8.94 (s, 1H, exchanges with D$_2$O, NH̲) and 10.7 (bs, 1H, exchanges with D$_2$O, NH̲); IR(KBr) 3317, 3223, 1707, 1618, 1532, 1463 , 1408, 1335, 1207, 1072, 1019, 931, 840 and 643 cm$^{-1}$; FDMS(MeOH) m/e=386 (M+). Anal Calcd for C$_{17}$H$_{17}$F$_3$N$_2$O$_3$S$_1$: C, 52.85; H, 4.44; N, 7.25. Found C, 52.75; H, 4.60; N, 6.99.

EXAMPLE 4

N-[[(3,4-Dichlorophenyl)amino]carbonyl]-3,4,5-trimethylbenzenesulfonamide

The method of Example 1 was followed using 3,4,5-trimethylbenzenesulfonamide (2.0 g, 10 mmol) , 1N NaOH solution (10 mL, 10 mmol) and 3,4-dichlorophenyl isocyanate (2.1 g, 11 mmol) to yield 2.4 g (61%) of product.

Analysis of the product gave the following results: mp=178–179° C.; $R_f$1/9 MeOH/CHCl$_3$)=0.53 ; $^1$H NMR (300 MHz, d$_6$ -DMSO) $\delta$2.17 ( s, 3H, CH$_3$), 2.30 (s, 6H, 2 CH$_3$), 7.26 (d, 1H, J=8.8 Hz, Ar—H̲), 7.48 (d, 1H, J=8.8 Hz, Ar—H̲), 7.55 (s, 2H, Ar—H̲), 7.65 (s, 1H, Ar—H̲), 9.12 (s, 1H, exchanges with D$_2$O, NH̲) and 10.9 (bs, 1H, exchanges with D$_2$O, NH̲); IR (KBr)3321, 3257, 1706, 1578, 1508, 1441, 1405, 1386, 1330, 1201, 1040, 905 and 668 cm$^{-1}$; FDMS (DMSO) m/e=386, 388 (M+) . Anal Calcd for C$_{16}$H$_{16}$Cl$_2$N$_2$O$_3$S$_1$: C, 49.62; H, 4.16; N, 7.23. Found C, 49.68; H, 4.21; N, 7.14.

EXAMPLE 5

3,4,5-Trichlorobenzenesulfonamide 3,5-Dichloro-4-aminobenzenesulfonamide (12.1 g, 50.2 mmol) was added to 150 mL of concentrated HCl; the thick suspension was cooled to 0° C. and, with vigorous stirring, treated with a solution of NaNO$_2$ (4.2 g, 60.9 mmol) in 20 mL of water, dropwise, over 15 min; the resulting orange diazonium salt mixture was slowly poured into a beaker containing CuCl (12.4 g, 125.5 mmol) and 100 mL of concentrated HCl at 0° C. (the reaction mixture foams and must be mechanically stirred). The stirred reaction mixture was warmed to room temperature for 1 h and then heated at 70° C. for 30 min. After cooling, the reaction mixture was extracted with CH$_2$Cl$_2$ (3×200 mL). The combined organic layers were dried over Na$_2$SO$_4$, filtered and concentrated to give 9.89 g of the product as a yellow solid. Silica gel flash chromatography (30%EtOAc/hexane) afforded 8.13 g (62%) of the sulfonamide as a white solid.

Analysis of the product gave the following results: mp=190–191° C.; $R_f$(1:1 EtOAc/hexane)=0.57; $^1$H NMR (300 MHz, d$_6$-DMSO) $\delta$7.68 (bs, 2H, exchanges with D$_2$O, NH̲$_2$) and 7.97 (s, 2H, Ar—H̲); IR(KBr) 3308, 2969, 1623, 1529, 1458, 1292, 1163, 1111, 976 and 842 cm$^{-1}$; FDMS (DMSO) m/e=259, 261, 263 (M+) . Anal Calcd for C$_6$H$_4$Cl$_3$N$_1$O$_2$S$_1$: C, 27.66; H, 1.55; N, 5.38. Found C, 27.87; H, 1.51; N, 5.09.

EXAMPLE 6

N-[[(4-Chlorophenyl)amino]carbonyl]-3,4,5-trichlorobenzene sulfonamide

The method of Example 1 was followed using 3,4,5-trichlorobenzenesulfonamide (2.6 g, 10 mmol), 1N NaOH solution (10 mL, 10 mmol) and p-chlorophenyl isocyanate (1.7 g, 11 mmol) to yield 3.59 g (87%) of product.

Analysis of the product gave the following results: mp=193–195° C.; $R_f$(5/95 MeOH/CH$_2$Cl$_2$)=0.24 ; $^1$H NMR (300 MHz, d$_6$-DMSO) $\delta$6.58 (s, 2H, exchanges with D$_2$O, NH̲$_2$), 7.31 (d, 2H, J=8.9 Hz, Ar—H̲), 7.37 (d, 2H, J=8.9 Hz, Ar—H̲)7.73 (s, 2H, Ar—H̲), 9.09 (s, 1H, exchanges with D$_2$O, NH̲)and 10.7 (bs, 1H, exchanges with D$_2$O, NH̲); IR(KBr) 3496, 3470, 3375, 3294, 1700, 1622, 1595, 1524, 1451, 1401, 1341, 1166, 1041, 925 and 672 cm$^{-1}$; FDMS (DMSO) m/e 392, 394, 396 (M+) . Anal Calcd for C$_{13}$H$_{10}$Cl$_3$N$_3$O$_3$S$_1$: C, 39.56; H, 2.55; N, 10.65. Found C, 39.64; H,2.55; N, 10.33.

EXAMPLE 7

N,[[(4-Chlorophenyl)amino]carbonyl]-4-amino-3,5-dichlorobenzenesulfonamide

The method of Example 1 was followed using 3,5-dichlorosulfanilamide (4.8 g, 20 mmol), 1N NaOH solution (40 mL, 40 mmol ) and p-chlorophenyl isocyanate (3.4 g, 22 mmol) to yield 6.68 g (85%) of product.

Analysis of the product gave the following results: mp=194–196° C.; $R_f$(1/9 MeOH/CHCl$_3$)=0.24 ; $^1$H NMR (300 MHz, d$_6$-DMSO) $\delta$7.2–7.4 (m, 4H, Ar—H̲), 8.09 (s, 2H, Ar—H̲), 9.35 (s, 1H, exchanges with D$_2$O, NH̲) and 10.5 (bs, 1H, exchanges with D$_2$O, NH̲); IR(KBr) 3373, 3262, 1706, 1601, 1537, 1455, 1403, 1374, 1344, 1198, 1155, 1034, 932, 822 and 674 cm$^{-1}$; UV-(EtOH) λmax(e) 207.2(48908) and 246.4(26033.7) nm; FDMS (DMSO) m/e 412, 414, 416, 418 (M+) . Anal Calcd for C$_{13}$H$_8$Cl$_4$N$_2$O$_3$S$_1$: C, 37.71; H, 1.95; N, 6.76. Found C, 37.84; H, 1.93; N, 6.67.

EXAMPLE 8

O-(4-Chloro-3,5-dimethylphenyl)-N,N-dimethylthiocarbamate

A 3-neck 500 mL round-bottom flask, fitted with a mechanical stirrer, thermometer, addition funnel and nitrogen purge, was charged with 4-chloro-3,5-dimethylphenol (15.7 g, 0.10 mol), KOH (6.6 g, 0.10 mol) and 120 mL of water. The mixture was stirred 10 min and than cooled to +10° C. N,N-Dimethylthiocarbamoyl chloride (16.4 g, 0.13 mol) dissolved in 40 mL of THF was added dropwise to the reaction mixture over 15 min. The resulting yellow slurry was stirred 30 min, then made basic with 1N NaOH solution. The solid product was filtered off, rinsed with 500 mL of water and taken up in 500 mL of EE. After washing with water (1×200mL) and brine (1×50 mL) the organic phase was dried over $MgSO_4$, filtered and evaporated to a yellow solid, 20.2 g (83%). An analytical sample was prepared by recrystallization from MeOH.

Analysis of the product gave the following results: mp=125–126° C.; $R_f$(3/7, EtOAc/hexane)=0.42; $^1$H NMR (300 MHz, $CDCl_3$) δ2.39 (s, 6H, 2$CH_3$), 3.33 and 3.47 (s, 6H, $NCH_3$) and 6.83 (s, 2H, Ar—H); IR(KBr) 2987, 1537, 1468, 1399, 1311, 1277, 1213, 1179, 1134, 1054 and 1028 $cm^{-1}$; UV(EtOH) λmax(e) 204.2(30099) and 251.2(13933) nm; FDMS (MeOH) m/e 243, 245 (M+). Anal Calcd for $C_{11}H_{14}Cl_1N_1O_1S_1$: C, 54.20; H, 5.79; N, 5.75. Found C, 54.45; H, 6.00; N, 5.86.

EXAMPLE 9

S-(4-Chloro-3,5-dimethylphenyl)-N,N-dimethylthiocarbamate

The O-(4-chloro-3,5-dimethylphenyl)-N,N-dimethylthiocarbamate (18.0 g, 74 mmol) was heated neat under nitrogen to a temperature of 250° C.; rearrangement to product was conveniently monitored by TLC (30% EtOAC/hexane) and was complete after 7 h. A small sample was purified by silica gel flash chromatography(3/7 EtOAC/hexane) to provide an analytical sample.

Analysis of this sample gave the following results: mp=99–100° C.; $R_f$(3/7, EtOAc/hexane)=0.28 ; $^1$H NMR (300 MHz, $CDCl_3$) δ2.39 (s, 6H, 2$CH_3$), 3.07 (bs, 6H, $NCH_3$) and 7.23 (s, 2H, Ar—H); IR(CHCl$_3$) 3012, 2929, 1657, 1368, 1262, 1101, 1052 and 909 $cm^{-1}$; UV-(EtOH) λmax(e) 207.8(30759) and 248.0 (8002) nm; FDMS (MeOH) m/e 243, 245 (M+). Anal Calcd for $C_{11}H_{14}Cl_1N_1O_1S_1$; C, 54.20; H, 5.79; N, 5.75. Found C, 54.47; H, 5.86; N, 6.02.

EXAMPLE 10

4-Chloro-3,5-dimethylthiophenol

The crude S-(4-chloro-3,5-dimethylphenyl)-N,N-dimethylthiocarbamate (17 g, 71 mmol) was dissolved in 200 mL of MeOH and 25 mL of water. KOH (16.8 g, 255 mmol) was added and the mixture was heated at reflux for 2 hr. After cooling and removal of the MeOH in vacuo, the residue was diluted with water (500 mL) and washed with EE (3×200 mL). The aqueous layer was acidified with conc. HCl and extracted with $CH_2Cl_2$ (3×100 mL); the combined organic extract was dried ($Na_2SO_4$), filtered and evaporated to yield 11 g of a dark oil. Vacuum distillation gave the product as a light yellow oil.

Analysis of the product gave the following results: bp=70–72° C. (0.25 mm Hg); $R_f$(1/9, EtOAc/hexanes)=0.44; $^1$H NMR (300 MHz, $CDCl_3$) δ2.34 ( s, 6H, 2$CH_3$), 3.38 (s, 1H, exchanges with $D_2O$, SH) and 7.02 (s, 2H, Ar—H); IR ($CHCl_3$) 3010, 2958, 2928, 1577, 1465, 1438, 1380, 1210, 1138, 1049 and 854 $cm^{-1}$; UV-(EtOH) λmax(e) 208.2(15887) and 247.4(7612) nm; FDMS (MeOH) m/e 342, 344 (M+) . Anal Calcd for $C_8H_9Cl_1S_1$: C, 55.65; H, 5.25. Found C, 55.49; H,5.32.

EXAMPLE 11

4-Chloro-3,5-dimethylbenzenesulfonamide

The 4-chloro-3,5-dimethylthiophenol (7.9 g, 46 mmol) was dissolved in 70 mL of glacial HOAc and chlorine gas was bubbled in beneath the surface of the solution over 30 min; the reaction temperature rose to 40° C. and the mixture turned red, then black and finally yellow in color. Solid material separated from solution after 2 h. After cooling to 0° C., water (125 mL) was added. The resulting solid sulfonyl chloride was collected by filtration and added to 50 mL of liquid ammonia at −78° C. After stirring 1 h, the cold bath was removed and the reaction mixture concentrated to a volume of about 20 mL in vacuo. Water (100 mL) was added and the slurry stirred for 30 min. The sulfonamide was collected by filtration, rinsed with water (2×100 mL) and EE (50 mL) and vacuum-dried overnight at 50° C. to yield 10 g (90%) of the product.

Analysis of the product gave the following results: mp=200–201° C.; $R_f$(1/1, EtOAc/hexane)=0.62; $^1$H NMR (300 MHz, $d_6$-DMSO) δ2.38 (s, 6H, 2$CH_3$), 7.33 (s, 2H, exchanges with $D_2O$, $NH_2$) and 7.61 (s, 2H, Ar—H); IR(KBr) 3354, 3260, 1321, 1284, 1155, 1118 and 1043 $cm^{-1}$; FDMS(MeOH) m/e (M+) . Anal Calcd for $C_8H_9Cl_1S_1$: C, 55.65; H, 5.25. Found C, 55.49; H,5.32.

EXAMPLE 12

N-[[(4-Chlorophenyl)amino]carbonyl]-4-chloro-3,5-dimethylbenzenesulfonamide

The method of Example 1 was followed using 4-chloro-3,5 -dimethylbenzenesulfonamide (1.2 g, 5.6 mmol), 1N NaOH solution (5.6 mL, 5.6 mmol ) and p-chlorophenyl isocyanate (981 mg, 6.4 mmol) to yield 1.3g (62%) of product.

Analysis of the product gave the following results: mp=186–189° C.; $R_f$(1/9, MeOH/CHCl$_3$)=0.48 ; $^1$H NMR (300 MHz, $d_6$-DMSO) δ2.40 (s, 6H, 2CH3), 7.30–7.38 (m, 4H, Ar—H), 7.7 5 (s, 2H, Ar—H), 9.07 (s, 1H, exchanges with $D_2O$, NH) and 10.9 (s, 1H, exchanges with $D_2O$, NH); IR(KBr) 3366, 1707, 1599, 1536, 1495, 1455, 1340, 1291, 1197, 1118, 1037, 929, 824 and 672 $cm^{-1}$; FDMS (MeOH) m/e 372, 374 (M+). Anal Calcd for $C_{15}H_{14}Cl_2N_2O_3S_1$: C, 48.27; H, 3.78; N, 7.51. Found C, 48.46; H, 3.89; N, 7.73.

EXAMPLE 13

3.5-Dichloro-4-(N,N-dimethylamino)benzenesulfonamide

This was prepared according to Org. Syn., 24, 47(1944) using 4-(dimethyl-amino)benzenesulfonamide[3] (4 g, 20 mmol) to give 1.96g (36%) of the product.

Analysis of the product gave the following results: mp =149–150° C.; $R_f$(1/1, EtOAc/hexane)=0.64 ; $^1$H NMR (300 MHz, $d_6$-DMSO) δ2.85 (s, 6H, 2$CH_3$), 7.5 (bs, 2H, exchanges with $D_2O$, $NH_2$) and 7.74 (s, 2H, Ar—H); IR(KBr) 3370, 3276, 2911, 2875, 2796, 1505, 1426, 1377, 1340, 1161, and 800 $cm^{-1}$; FDMS(MeOH)

m/e 268, 270 (M+). Anal Calcd for $C_{15}H_{14}Cl_2N_2O_3S_1$: C, 35.70; H, 3.74; N, 10.41. Found C, 35.43; H, 3.58; N, 10.28.

EXAMPLE 14

N-[[(4-Chlorophenyl)amino]carbonyl]-4-(N,N-dimethylamino)-3,5-dichlorobenzene-sulfonamide The method of Example 1 was followed using 3,5-dichloro-4-(N,N-dimethyl-amino)benzenesulfonamide (1.9 g, 7.1 mmol ), 1N NaOH solution (7.1 mL, 7.1 mmol ) and p-chlorophenyl isocyanate (1.3 g, 8.5 mmol) to yield 1.95 g (65% ) of product.

Analysis of the product gave the following results: mP=182-183° C.; $R_f(1/9$, MeOH/CHCl$_3$)=0.38; $^1$NMR (300 MHz, d$_6$-DMSO) $\delta$2.88 (s, 6H, 2CH$_3$), 7.29-7.39 (m, 4H, Ar—H), 7.85 (s, 2H, Ar—H), 9.24 (s, 1H, exchanges with D$_2$O, NH) and 10.95 (bs, $^1$H, exchanges with D$_2$O, NH); IR(KBr) 3381, 3282, 2923, 1722, 1604, 1541, 1454, 1339, 1164, 1012, 955, 829, 801 and 676 cm$^{-1}$; FDMS (MeOH) m/e 421, 423, 425(M+). Anal Calcd for $C_{15}H_{14}Cl_3N_3O_3S_1$: C, 42.62; H, 3.34; N, 9.94. Found C, 42.83; H, 3.32; N, 10.04.

EXAMPLE 15

N-[[(4-Chlorophenyl)amino]carbonyl]-3,5-dimethyl-4-methoxybenzesulfonamide

The method of Example 1 was followed using 3,5-dimethyl-4-methoxybenzenesulfonamide[4] (3.2 g, 15 mmol), 1N NaOH solution (15 mL, 15 mmol) and p-chlorophenyl isocyanate (2.5 g, 16 mmol) to yield 4.12 g (75%) of product.

Analysis of the product gave the following results: mp=175-176.5° C.; $R_f(1/9$, MeOH/CHCl$_3$)=0.61 ; $^1$H NMR (300 MHz, d$_6$-DMSO) $\delta$2.27 (s, 6H, 2CH$_3$), 3.70 (s, 3H, OCH$_3$), 7.27-7.37 (m, 4H, Ar—H), 7.62 (s, 2H, Ar—H), 8.97 (s, 1H, exchanges with D$_2$O, NH) and 10.71 (bs, 1H, exchanges with D$_2$O, NH); IR (KBr) 3373, 3235, 1715, 1601, 1540, 1495, 1334, 1280, 1196, 1146, 1006, 936, 827 and 672 cm$^{-1}$; FDMS(MeOH) m/e 368, 370 (M+). Anal Calcd for $C_{16}H_{17}Cl_1N_2O_4S_1$: C, 52.10; H, 4.65; N, 7.60. Found C, 52.31; H, 4.71; N, 7.62.

EXAMPLE 16

N-[[(4-Chlorophenyl)amino]carbonyl]-3,4,5-trimethoxylbenzenesulfonamide

The method of Example 1 was followed using 3,4,5-trimethoxybenzenesulfonamide[5] (1.1 g, 4.5 mmol ), 1N NaOH solution (4.5 mL, 4.5 mmol) and p-chlorophenyl isocyanate (750 mg, 4.9 mmol) to yield 1.46g (82%) of product.

Analysis of the product gave the following results: mp=190-191° C.; $R_f(1/9$ MeOH/CHCl$_3$)=0.37; $^1$H NMR (300 MHz, d$_6$-DMSO) $\delta$3.72 (s, 3H, OCH$_3$), 3.82 (s, 6H, 2OCH$_3$), 7.22 (s, 2H, Ar—H) 7.28-7.38 (m, 4H, Ar—H), 9.08 (s, 1H, exchanges with D$_2$O, NH) and 10.78 (bs, 1H, exchanges with D$_2$O, NH); IR(KBr) 3312, 3208, 1699, 1527, 1456, 1343, 1232, 1160, 1101, 1038, 1013, 930, 826 and 673 cm$^{-1}$; FDMS (DMSO) m/e 400, 402 (M+). Anal Calcd for $C_{16}H_{17}Cl_1N_2O_5S_1$: C, 47.94; H, 4.27; N, 6.99. Found C, 47.74; H, 4.24; N, 6.54.

EXAMPLE 17

3,5 -Dibromo-4-N-methylamino)benzenesulfonamide

This was prepared according to Org. Syn., 24, 47(1944) using 4-(dimethylamino)benzenesulfonamide[3] (10 g, 50 mmol) to give 6.28 g (37%) of the monoalkylated product.

Analysis of the product gave the following results: mp=186-187° C.; $R_f(1/1$, EtOAc/hexane)=0.46; $^1$H NMR (300 MHz, d$_6$-DMSO) $\delta$3.02 (d, 3H, NCH$_3$), 5.41 (bd, $^1$H, exchanges with D$_2$O, NH), 7.31 (s, 2H, exchanges with D$_2$O, NH$_2$) and 7.81 (s, 2H, Ar—H); IR(KBr) 3319, 3282, 1573, 1476, 1331, 1163, and 1120 cm$^{-1}$; FDMS (MeOH) m/e 342, 344, 346 (M+). Anal Calcd for $C_7H_8Br_2N_2O_2S_1$: C, 24.44; H, 2.34; N, 8.14. Found C, 24.42; H, 2.31; N, 8.08.

EXAMPLE 18

N-[[(4-Chlorophenyl)amino]carbonyl]-3,5-dibromo-4-(N-methylamino)benzenesulfonamide The method of Example 1 was followed using 3,5-dibromo-4-(N-methyl-amino)benzenesulfonamide (3.4 g, 10 mmol), 1N NaOH solution (10 mL, 10 mmol) and p-chlorophenyl isocyanate (1.8 g, 12 mmol) to yield 3.27 g (66%) of product.

Analysis of the product gave the following results: mp=186-187° C.; $R_f(1/9$, MeOH/CHCl$_3$)=0.45; $^1$H NMR (300 MHz, d$_6$-DMSO) $\delta$3.10 (s, 3H, NCH$_3$), 5.76 (bs, 1H, exchanges with D$_2$O, NH), 7.29-7.38 (m, 4H, Ar—H), 7.91 (s, 2H, Ar—H), 9.14 (s, 1H, exchanges with D$_2$O, NH) and 10.75 (bs, 1H, exchanges with D$_2$O, NH); IR(KBr) 399, 3359, 3220, 1675, 1601, 1535, 1492, 1401, 1356, 1169, 1033, 906, 830 and 668 cm$^{-1}$; FDMS (MeOH) m/e 495, 497, 499 (M+) . Anal Calcd for $C_{14}H_{12}Br_2ClN_3O_3S$: C, 33.79; H, 2.43; N, 8.44. Found C, 33.60; H, 2.38; N, 8.37.

The following are the references cited in the Examples:

1. Howbert, J. J.: Grossman, S. C.; Crowell, T. A.; Rieder, B. J.; Harper, R. W.; Kramer, K. E.; Tao, E. V.; Aikins, J.; Poore, G. A.; Rinzel, S. M.; Grindey, G. B.; Shaw, W. N.; Todd, G. C. J. Med. Chem. 1990, 33, 2393.
2. Holt, G., Pagdin, B. J. Chem. Soc. 1961, 4514.
3. Blank, B.; Farina, F. A.; Kerwin, J. F.; Saunders, H. J. Org. Chem. 1961, 26, 1552.
4. Takimoto, H. H.; Danault, G. C. J. Org. Chem. 1964, 29, 759.
5. Pifferi, G.; Monguzzi, R. J. Pharm. Sci. 1973, 62, 1392.

The compounds of Formula I have been shown to be active against transplanted mouse tumors in vivo. The compounds were tested in C3H mice bearing a 6C3HED lymphosarcoma, also known as the Gardner lymphosarcoma (GLS). The 6C3HED lymphosarcoma was obtained from the Division of Cancer Treatment, National Cancer Institute, Tumor Bank, maintained at E. G. and G. Mason Research (Worcester, Mass.). First passage tumor was stored in liquid nitrogen using standard techniques. The transplanted tumor was reestablished from the Tumor Bank every six months or as needed. The tumor was maintained by serial passage twice weekly in C3H mice.

In the procedure the tumor was removed from passage animals and minced into 1- to 3-mm square fragments using sterile techniques. Tumor pieces were checked for sterility using both Antibiotic Medium 1 and Brain Heart Infusion (Difco, Detroit, Mich.). Recipient mice were shaved and tumor pieces were implanted subcutaneously in the auxiliary region by trocar. Drug therapy on the appropriate schedule was initiated on the day after tumor implant. The compound being tested was mixed with 2.5 weight % of a polyoxyethylated oil known as "Emulphor EL-620" surfactant from GAF Chemicals Corporation (1:40 dilution of Empulphor in saline). All animals were weighed at the beginning and end of administration of the subject compounds. Food and water were provided ad libitum. The drug was administered orally in 0.5 ml of 2.5% Emulphor. Unless otherwise indicated, the compound was administered once per day for eight days. The tumor was measured the day after treatment ended with two dimensional measurements (width and length) of the tumor taken using Vernier calipers. Tumor weights were calculated from these measurements using the following formula:

(tumor weight in mg)=(width in mm)$^2$×(length in mm)/2

At least one control group of an equal number of mice was treated with the same volume of 2.5% Emulphor only. The percent inhibition was calculated by subtracting the ratio of the mean tumor size of the test group relative to the control group from 1 and multiplying the result by 100.

The results of administering some of the present compounds orally (unless otherwise indicated) to mice bearing a 6C3HED tumor are provided in the Table. In the Table, column 1 gives the example number corresponding to the preparation of the particular compound, column 2 provides the dose level, column 3 lists the percent inhibition of tumor growth, and column 4 gives the number of mice which died relative to the total number of animals in the group.

The in vitro CCRF-CEM data reported in column 5 of the Table was obtained using CCRF-CEM cells, a human leukemia cell line, (Foley et al., Cancer, 1965, 18, 522) were grown as previously described (Grindey, et al., J. Mol. Pharmacol., 1979, 16, 601) both references incorporated herein by reference. Dose-response curves were generated for various compounds to determine the concentration required for 50% inhibition of growth (IC$_{50}$). Cluster plates were prepared in duplicate with the compound at various concentrations. Test compounds were dissolved initially in DMSO at a concentration of 4 mg/mL and further diluted with solvent to the desired concentration. Cells in Roswell Park Memorial Institute 1640 media supplemented with 10% dialyzed fetal bovine serum, and 25 mM HEPES buffer were added to the well an a final concentration of 4.8×10$^4$ cells/well in a total volume of 2.0 mL. After 72 h of incubation (95% air, 5% CO$_2$), cell numbers were determined on a ZBI Coulter counter. Cell number for indicated controls at the end of incubation was usually (4–6)×10$^5$ cells/well.

TABLE

| Example No. | Dosing (1) Level mg/kg | % Tumor (2) Inhibition | Toxic/ Total (3) | in vitro (4) (CCRF-CEM) IC$_{50}$ μg/ml |
|---|---|---|---|---|
| 1 | 300 | 100 | 0/10 | 14.8 |
|   | 150 | 99  | 0/10 |      |
| 2 | 300 | 99  | 8/10 | >20  |
|   | 150 | 99  | 1/10 |      |
| 3 | 300 | 100 | 4/10 | >20  |
|   | 150 | 100 | 0/10 |      |
| 4 | 300 | 74  | 1/10 | 13.5 |
|   | 150 | 38  | 0/10 |      |
| 6 | 300 | 99  | 3/10 | >20  |
|   | 150 | 99  | 0/10 |      |
| 7 | 300 | Toxic | 10/10 | >20 |
|   | 150 | 95  | 0/10 |      |
| 12 | 300 | 84 | 1/10 | 15  |

TABLE -continued

| Example No. | Dosing (1) Level mg/kg | % Tumor (2) Inhibition | Toxic/ Total (3) | in vitro (4) (CCRF-CEM) IC$_{50}$ μg/ml |
|---|---|---|---|---|
|    | 150 | 44 | 0/10 |      |
| 14 | 300 | 93 | 0/10 | 17   |
|    | 150 | 50 | 1/10 |      |
| 15 | 300 | 87 | 0/10 | 16.5 |
|    | 150 | 55 | 1/10 |      |
| 16 | 300 | 35 | 0/10 | >20  |
|    | 150 | 6  | 0/10 |      |
| 18 | 300 | 47 | 0/10 | 19.3 |
|    | 150 | 26 | 1/10 |      |

(1) Dose in milligrams per kilogram of body weight administered orally daily for eight days.
(2) [1 − (mean tumor weight in test group/mean tumor weight in control group] × 100.
(3) Number of mice which died during test period/total number of mice in test group.
(4) in vitro cytoxicity against CCRF-CEM cells.

The compounds of Formula I are antineoplastic agents and the invention provides a method of treating susceptible neoplasms in mammals, particularly humans. The method comprises administering a compound by various routes including the oral, rectal, transdermal, subcutaneous, intravenous, intramuscular, or intranasal routes, being usually employed in the form of a pharmaceutical composition. It is a special feature of these compounds that they are effective following oral administration. It has been found that higher dosage levels can be obtained by oral administration than by direct systemic administration due to a higher toxic effect observed with systemic administration.

The present compounds are useful in treating solid tumors including carcinomas such as ovarian, non-small cell lung, gastric pancreatic, prostrate, renal cell, breast, colorectal, small cell lung, melanoma and head and neck, and sarcomas such as Kaposi's sarcoma and rhabdomyosarcoma.

The instant compounds can be administered individually or in combination, preferably orally, and usually in the form of a pharmaceutical composition. Such compositions are prepared in a manner well known in the pharmaceutical art and comprise at least one active compound. Accordingly, the present invention also includes pharmaceutical compositions comprising as active ingredient certain compounds of Formula I associated with a pharmaceutically acceptable carrier, and the invention further comprises the method of treating susceptible neoplasms using the compositions containing as an active ingredient a compound of Formula I.

In making the compositions of the present invention, as well as compositions containing other compounds of Formula I, the active ingredients are usually mixed with an excipient, diluted by an excipient or enclosed within such a carrier which can be in the form of a capsule, sachet, paper or other container. When the excipient serves as a diluent, it may be a solid, semi-solid or liquid material which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

In preparing a formulation it may be necessary to mill the active compound to provide the appropriate particle size prior to combining with the other ingredients. If the active compound is substantially insoluble, it ordinarily is milled to a particle size of less than about 200 mesh. If the active compound is substantially water soluble, the particle size is normally adjusted by milling to provide a substantially uniform distribution in the formulation, e.g., about 40 mesh. Some examples of suitable excipients include lactose, dextrose, sucrose, sorbitol, mannitol, starches, gum aracia, calcium silicate, microcrystalline cellulose, polyvinylpyrrolidone, cellulose, water, syrup, and methyl cellulose. The formulations can additionally include lubricating agents such as talc, magnesium stearate and mineral oil, wetting agents, emulsifying and suspending agents, preserving agents such as methyl- and propylhydroxybenzoates, sweetening agents or flavoring agents. The compositions of the invention can be formulated so as to provide quick, sustained or delayed release of the active ingredient after administration to the patient by employing procedures well known in the art.

The compositions are preferably formulated in a unit dosage form with each dosage normally containing from about 5 mg to about 1 g, more usually about 25 to about 800 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are effective over a wide dosage range. For example, dosages per day will normally fall within the range of about 0.5 to about 1200 mg/kg of body weight. In the treatment of adult humans, the range of about 1 to about 50 mg/kg, in single or divided doses, is preferred. However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms, and therefore the above dosage ranges are not intended to limit the scope of the invention in any way.

The following formulation examples may employ as active compounds any of the compound of Formula 1. The examples are illustrative only and are not intended to limit the scope of the invention in any way.

Formulation 1

Hard gelatin capsules are prepared using the following ingredients:

|  | Quantity (mg/capsule) |
| --- | --- |
| Example 1 | 250 |
| Starch | 305 |
| Magnesium stearate | 5 |

The above ingredients are mixed and filled into hard gelatin capsules in 560 mg quantities.

Formulation 2

A tablet formula is prepared using the ingredients below:

|  | Quantity (mg/capsule) |
| --- | --- |
| Example 2 | 250 |
| Cellulose, microcrystalline | 400 |
| Colloidal silicon dioxide | 10 |
| Stearic acid | 5 |

The components are blended and compressed to form tablets each weighing 665 mg.

Formulation 3

Tables each containing 60 mg of active ingredient are made up as follows:

|  |  |
| --- | --- |
| Example 3 | 60 mg |
| Starch | 45 mg |
| Microcrystalline cellulose | 35 mg |
| Polyvinylpyrrolidone (as 10% solution in water | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 20 mesh U.S. sieve and mixed thoroughly. The solution of polyvinylpyrrolidone is mixed with the resultant powders which are then passed through a No. 4 mesh U.S. sieve. The granules so produced are dried at 50-60° C. are passed through a No. 16 mesh U.S. sieve. The sodium carboxymethyl starch, magnesium stearate and talc, previously passed through a No. 30 mesh U.S. sieve, are then added to the granules which, after mixing, are compressed on a tablet machine to yield tablets each weighing 150 mg.

Formulation 4

Capsules each containing 80 mg of medicament are made as follows:

|  |  |
| --- | --- |
| Example 4 | 80 mg |
| Magnesium stearate | 109 mg |
| Magnesium stearate | 1 mg |
| Total | 190 mg |

The active ingredient, starch and magnesium stearate are blended, passed through a No. 20 mesh U.S. sieve, and filled into hard gelatin capsules in 190 mg quantities.

Formulation 5

Suppositories each containing 225 mg of active ingredient are made as follows:

|  |  |
| --- | --- |
| Example 6 | 225 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 6

Suspensions each containing 50 mg of medicament per 5 ml dose are made as follows:

| Example 7 | 50 mg |
| --- | --- |
| Xanthan gum | 4 mg |
| Sodium carboxymethyl cellulose (11%) Microcrystalline cellulose (89%) | 50 mg |
| Sucrose | 1.75 g |
| Sodium benzoate | 10 mg |
| Flavor | q.v. |
| Color | q.v. |
| Purified water to | 5 ml |

The medicament, sucrose and xanthan gum are blended, passed through a No. 10 mesh U.S. sieve and then mixed with a previously made solution of the microcrystalline cellulose and sodium carboxymethyl cellulose in water. The sodium benzoate, flavor and color are diluted with some of the water and added with stirring. Sufficient water is then added to produce the required volume.

Formulation 7

Capsules each containing 150 mg of medicament are made as follows:

| Example 12 | 150 mg |
| --- | --- |
| Starch | 407 mg |
| Magnesium stearate | 3 mg |
| Total | 560 mg |

The active ingredient, starch and magnesium stearate are blended, passed through a No. 20 mesh U.S. sieve, and filled into hard gelatin capsules in 560 mg quantities.

Formulation 8

A dry powder inhaler formulation is prepared containing the following components:

| Example 14 | 5 |
| --- | --- |
| Lactose | 95 |

The active compound is mixed with the lactose and the mixture added to a dry powder inhaling appliance.

We claim:

1. A compound useful in the treatment of susceptible neoplasms in mammals having the formula

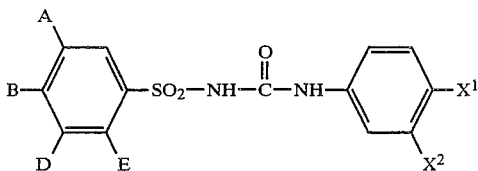

wherein $X^1$ is halo, $CH_3$ or $CF_3$;

$X^2$ is hydrogen, halo, or $CF_3$ with the proviso that at least one of $X^1$ and $X^2$ is halo;

A, B, D and E are (a) independently selected from the group consisting of hydrogen, methoxyl, methyl, ethyl, chlorine, bromine and iodine with the proviso that no more than one of A, B, D or E is hydrogen and pharmaceutically acceptable salts thereof.

2. The compound of claim 1 wherein $X^1$ is chlorine, bromine or $CF_3$; $X^2$ is hydrogen or chlorine; A, B and D are independently methyl, ethyl or chlorine; E is hydrogen; and pharmaceutically acceptable salts thereof.

3. The compound of claim 1 selected from the group consisting of N-[[(4-chlorophenyl)amino]carbonyl]-3,4,5-trimethylbenzene sulfonamide; N-[[(4-bromophenyl)amino]carbonyl]-3,4,5-trimethylbenzenesulfonamide; N-[[(4-Trifluoromethylphenyl)amino]carbonyl]-3,4,5-trimethylbenzenesulfonamide; N-[[(3,4-dichlorophenyl)amino]carbonyl]-3,4,5-trimethylbenzenesulfonamide; N-[[(4-chlorophenyl)amino]carbonyl]-3,4,5-trichlorobenzene sulfonamide; N-[[(4-chlorophenyl)amino]carbonyl]-4-chloro-3,5-dimethylbenzenesulfonamide; N-[[(4-chlorophenyl)amino]carbonyl]-3,5-dimethyl-4-methoxybenzenesulfonamide; N-[[(4-chlorophenyl)amino]carbonyl]-3,4,5-trimethoxylbenzenesulfonamide; and pharmaceutically acceptable salts thereof.

4. The compound of claim 1 which is N-[[(4-chlorophenyl)amino]carbonyl]-3,4,5-trimethylbenzenesulfonamide.

5. The compound of claim 1 which is N-[[(4-trifluoromethylphenyl)amino]carboxyl]-3,4,5-trimethylbenzenesulfonamide.

6. The compound of claim 1 which is N-[[(4-chlorophenyl)amino]carbonyl]-3,4,5-trichlorobenzenesulfonamide.

7. A pharmaceutical formulation comprising a compound of claim 1 in combination with a pharmaceutically acceptable excipient.

8. The formulation of claim 7 wherein said compound is selected from the group consisting of N-[[(4-chlorophenyl)amino]carbonyl]-3,4,5-trimethylbenzene sulfonamide; N-[[(4-Bromophenyl)amino]-carbonyl]-3,4,5-trimethylbenzenesulfonamide; N-[[(4-Trifluoromethylphenyl)amino]carbonyl]-3,4,5-trimethylbenzenesulfonamide; N-[[(3,4-Dichlorophenyl)-amino]carbonyl]-3,4,5-trimethylbenzenesulfonamide; N-[[(4-Chlorophenyl)amino]carbonyl]-3,4,5-trichlorobenzene sulfonamide; N-[[(4-Chlorophenyl)amino]-carbonyl]-4-chloro-3,5-dimethylbenzenesulfonamide; N-[[(4-Chlorophenyl)amino]carbonyl]-3,5-dimethyl-4-methoxybenzenesulfonamide; N-[[(4-Chlorophenyl)amino]carbonyl]-3,4,5-trimethoxylbenesulfonamide; and pharmaceutically acceptable salts thereof.

* * * * *